United States Patent [19]

Nakajima et al.

[11] Patent Number: 4,963,246
[45] Date of Patent: Oct. 16, 1990

[54] OXYGEN CONCENTRATION-SENSING DEVICE

[75] Inventors: Toyohei Nakajima; Toshiyuki Mieno; Yasuhiro Toyoda; Haruo Horiuchi, all of Wako, Japan

[73] Assignee: Honda Giken Kogyo Kabushiki Kaisha, Tokyo, Japan

[21] Appl. No.: 284,285

[22] Filed: Dec. 14, 1988

[30] Foreign Application Priority Data

Dec. 14, 1987 [JP] Japan .................................. 62-316567
Dec. 14, 1987 [JP] Japan .................................. 62-316568
Aug. 26, 1988 [JP] Japan .................................. 63-212695

[51] Int. Cl.$^5$ .......................................... G01N 27/409
[52] U.S. Cl. ..................................... 204/406; 204/408; 219/499
[58] Field of Search ................. 204/406, 408, 1 S; 219/497, 499

[56] References Cited

U.S. PATENT DOCUMENTS

| | | |
|---|---|---|
| 3,946,198 | 3/1976 | Foote .................................... 219/497 |
| 4,384,934 | 5/1983 | de Bruin et al. ..................... 204/406 |
| 4,471,648 | 9/1984 | Uchida et al. ......................... 73/23 |
| 4,601,809 | 7/1986 | Kitahara ............................... 204/406 |
| 4,708,777 | 11/1987 | Kuraoka ............................... 204/1 T |
| 4,761,539 | 8/1988 | Carmean ............................... 219/497 |

Primary Examiner—G. L. Kaplan
Attorney, Agent, or Firm—Pollock, Vande Sande & Priddy

[57] ABSTRACT

An oxygen concentration-sensing device has an oxygen concentration-sensing element which senses the concentration of oxygen contained in a gas, and a heater which heats the sensing element. A control device is electrically connected to the heater for controlling the supply of electricity to the heater so as to bring the temperature of the heater to a desired temperature. A coupler connects between the sensing element and the control device. A compensating resistance is accommodated in the coupler, which has a resistance value corresponding to a resistance value of the heater assumed at the desired temperature. The control device controls the supply of electricity to the heater based upon electrical information obtained from the compensating resistance.

17 Claims, 10 Drawing Sheets

FIG. I

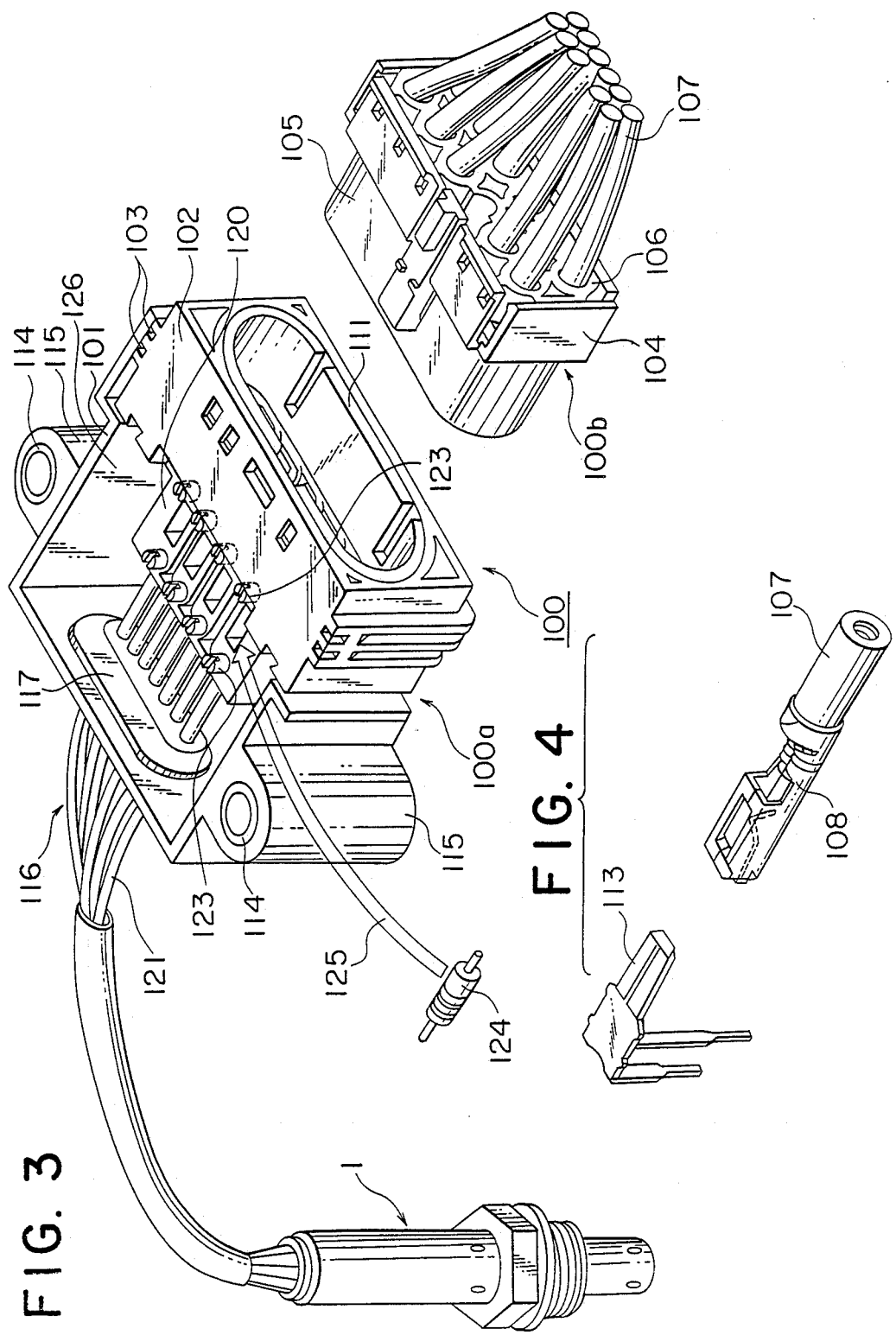

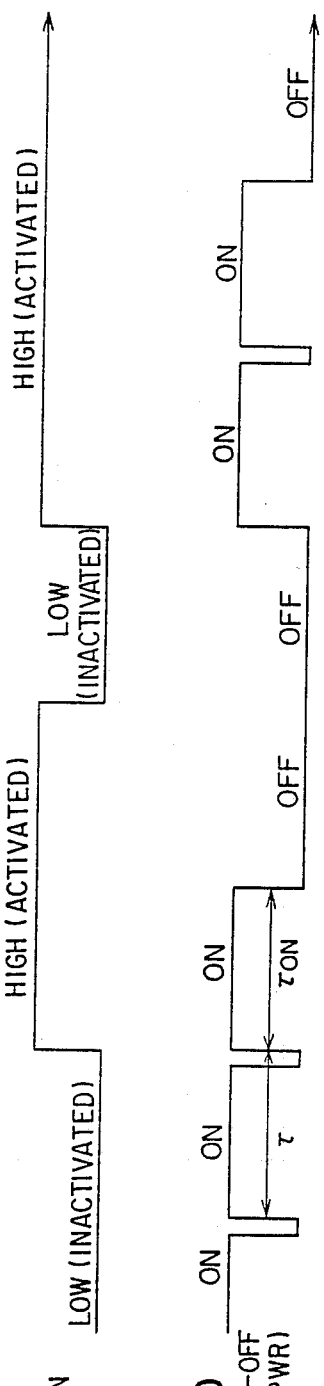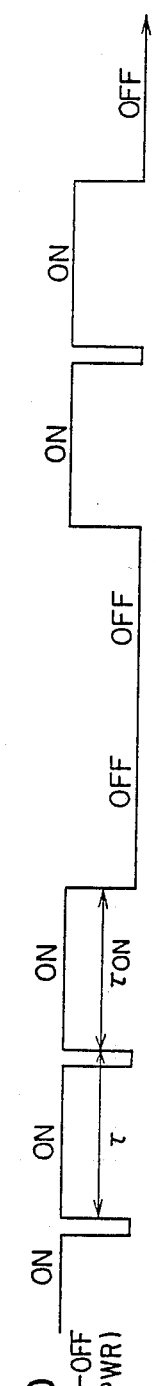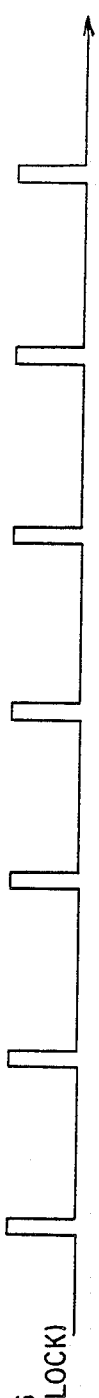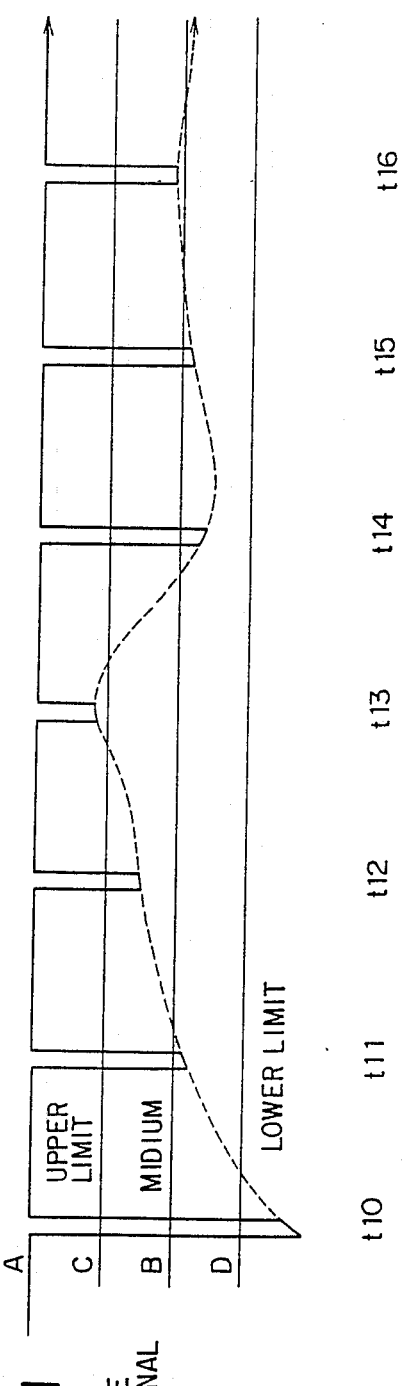

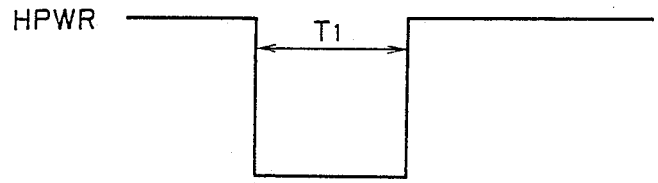
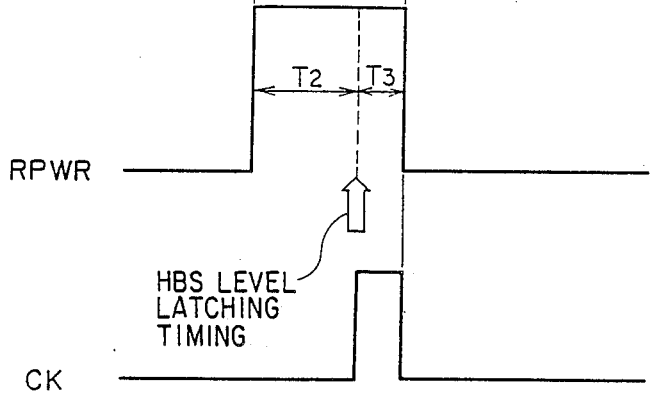
FIG. 8a HEATER POWER
FIG. 8b REFERENCE POWER
FIG. 8c CLOCK

OXYGEN CONCENTRATION-SENSING DEVICE

BACKGROUND OF THE INVENTION

This invention relates to an oxygen concentration-sensing device mainly intended for use in internal combustion engines for automotive vehicles, and more particularly to an oxygen concentration-sensing device of this kind which has a heater for heating the body of a sensor thereof.

It is well known to sense the concentration of oxygen in exhaust gases emitted from an internal combustion engine for automotive vehicles, and control the air-fuel ratio of a mixture supplied to the engine in a feedback manner responsive to the sensed oxygen concentration.

An oxygen concentration-sensing device of this kind is known e.g., from Japanese Provisional Patent Publication (Kokai) No. 61-35347, which has an oxygen concentration sensor provided with a heater which serves to promote the oxygen ion-conductivity of a solid electrolyte material forming the sensor body and hence enhance the electromotive characteristic of same.

According to the known device, a bridge circuit is used for controlling the resistance value of the heater to a predetermined value and hence the temperature of the sensor body to a desired value, in order to achieve accurate detection of the air-fuel ratio of the mixture.

However, in the known device, variation in resistance value between individual heaters used causes variation in temperature between the individual heaters and hence variation in temperature between individual sensor bodies, which results in variation in the output between individual sensors. The variation in resistance value mainly takes place during the manufacture of the heaters.

Particularly in a sensor of the proportionaloutput type which generates an output varying in proportion to the oxygen concentration, the variation in the heater resistance value exerts a great influence upon the output charateristic of the sensor, in that the sensor output is largely different between individual sensors even if they are heated to the same temperature. As a result, it is impossible to effect proper air-fuel ratio control.

Another is also known an oxygen concentrationsensing device from Japanese Provisional Patent Publication (Kokai) No. 57-20394-0, which, circuit formed by a heater for heating a sensor body, a first resistance provided on the heater side, and second and third resistances provided on the side of a temperature control circuit, wherein imbalance in potential of the bridge circuit is detected, and a voltage supplied to the heater is controlled depending upon the detected imbalance, so as to control the temperature of the sensor to a target value. According to this device, a resistance having a resistance value corresponding to the temperature vs. current characteristic of the heater, e.g., a resistance value $RH^o$ of the heater at room temperature, is selected as the first resistance so that the temperature of the heater and hence the sensor can be maintained at a target value, even if there is variation in temperature vs. current characteristic between individual heaters.

However, in the known oxygen concentrationsensing device, the resistance value of the first resistance has to be set at a value K (constant value) times as large as the resistance value of the heater at room temperature, that is, the former should be proportional to the latter. Further, the maximum allowable range of variation in the temperature vs. current characteristic between individual heaters of this kind is small. Therefore, the first resistance sometimes has to be selected from among ones with special values. To this end, it is necessary to use custom-made resistances with special resistance values, resulting in high manufacturing costs.

SUMMARY OF THE INVENTION

It is therefore the primary object of the invention to provide an oxygen concentration-sensing device which is capable of maintaining the temperature of a heater provided in an oxygen concentration sensor thereof at a desired value, regardless of variation in resistance value, i.e., current vs. temperature characteristic, between individual heaters.

It is a further object of the invention to eliminate variation in current vs. temperature characteristic of heaters by the use of easily obtainable component parts.

It is another object of the invention to prevent an oxygen concentration sensor from being damaged by excessively energizing the heater of the sensor both when the sensor is in a low-temperature inactivated state and in a high-temperature activated state.

To achieve the above objects, the present invention provides an oxygen concentration-sensing element for sensing the concentration of oxygen contained in a gas, a heater for heating the element, control means electrically connected to the hater for controlling the supply of electricity to the heater so as to bring the temperature of the heater to a desired temperature, and a coupler connecting the oxygen concentration-sensing element and the control means.

The oxygen concentration-sensing device according to the invention is characterized by an improvement comprising a compensating resistance accommodated in the coupler and having a resistance value corresponding to a resistance value of the heater at the desired temperature, and wherein the control means controls the supply of electricity to the heater based upon electrical information obtained from the compensating resistance.

Preferably, the coupler comprises a first connector connectible to the oxygen concentrationsensing element, and a second connector disconnectably mated with the first connector connectible to the control means, the compensating resistance being accommodated within the first connector.

More preferably, the oxygen device includes resin filled within the coupler in which the correcting resistance is buried.

In one embodiment of the invention, the compensating resistance and the heater cooperate to form part of a bridge circuit, the control means controlling the supply of electricity to the heater depending upon a reference voltage created by the compensating resistance and a voltage created by the heater.

In another embodiment of the invention, the device includes means for applying a given level of voltage to the compensating resistance, and wherein the control means comprises means for supplying electricity to the heater, means for reading in electrical information obtained from the compensating resistance when the given level of voltage is applied thereto, and electrical information obtained from the heater when supplied with the electricity, as second data and third data, respectively, means for correcting the second data by the first data, and means for determining the amount of electricity to be supplied to the heater from the corrected second data.

Preferably, the embodiment of the preceding paragraph includes a second resistance serially connected to the compensating resistance, and means for applying a given level of voltage to the compensating resistance and the second resistance, and wherein the control means comprises means for supplying electricity to the heater, means for reading in information on a voltage developed at a junction between the compensating resistance and the second resistance when the given level of voltage is applied thereto, and an amount of current flowing through the heater and a voltage developed across the heater when supplied with the electricity, as first data and second data, respectively means for calculating a resistance value of the heater from the second data read in, means for correcting one of the resistance value calculated and a reference resistance value assumed by the heater at the desired temperature by the first data read in, and means for determining a duty ratio corresponding to a difference between the corrected one of the resistance value calculated and the reference resistance value, and the other of same, and wherein the means for supplying electricity to the heater supplies electricity to the heater in an amount determined by the duty ratio so determined.

Preferably, the control means may have a map comprising a plurality of resistance values corresponding respectively to a plurality of predetermined resistance values which can be assumed by the hater at a predetermined temperature and a resistance value assumed by a reference heater at the predetermined temperature, and a plurality of correction values corresponding respectively to the plurality of resistance values, a resistance having a resistance value corresponding to a difference between an actual resistance value of the heater at the predetermined temperature and the resistance value of the reference heater at the predetermined temperature is selected as the compensating resistance from the map.

More preferably, the plurality of resistance values corresponding respectively to the predetermined differences may be set at legally prescribed standard resistance values.

According to another embodiment of the invention, the control means comprises a current supply means for supplying current to the heater, a bridge circuit composed of comparator for controlling the current supply means and having two input terminals, a first series circuit formed by the heater and a first resistance serially connected to the heater, a junction between the heater and the first reference resistance being connected to one of the input terminals of the comparator, a second series circuit formed by second and third resistances and connected in parallel with the first series circuit, a junction between the second and third resistances being connected to the other of the input terminals of the comparator, the compensating resistance comprising a fourth resistance connected in parallel to one of the second and third resistances.

Preferably, the compensating resistance may have a resistance value corresponding to a difference between an actual resistance value assumed by the heater at a predetermined temperature and a resistance value assumed by a reference heater at the predetermined temperature.

BRIEF DESCRIPTION OF THE DRAWINGS

The above and other objects, features, and advantages of the invention will be more clearly understood from the ensuing detailed description to be read with reference to the accompanying drawings.

FIG. 3 is an exploded perspective view of a coupler for connecting an $O_2$ sensor and an ECU of the device of FIG. 2;

FIG. 4 is a perspective view of connecting terminals used in the coupler of FIG. 3;

FIGS. 7A-D depict a timing chart of various signals generated in the heater control circuit of FIG. 6;

FIGS. 8A-C depict a diagram showing the relationship in timing between signals HPWR, RPWR, and CK generated in the heater control circuit of FIG. 6;

DETAILED DESCRIPTION

Figure 1:
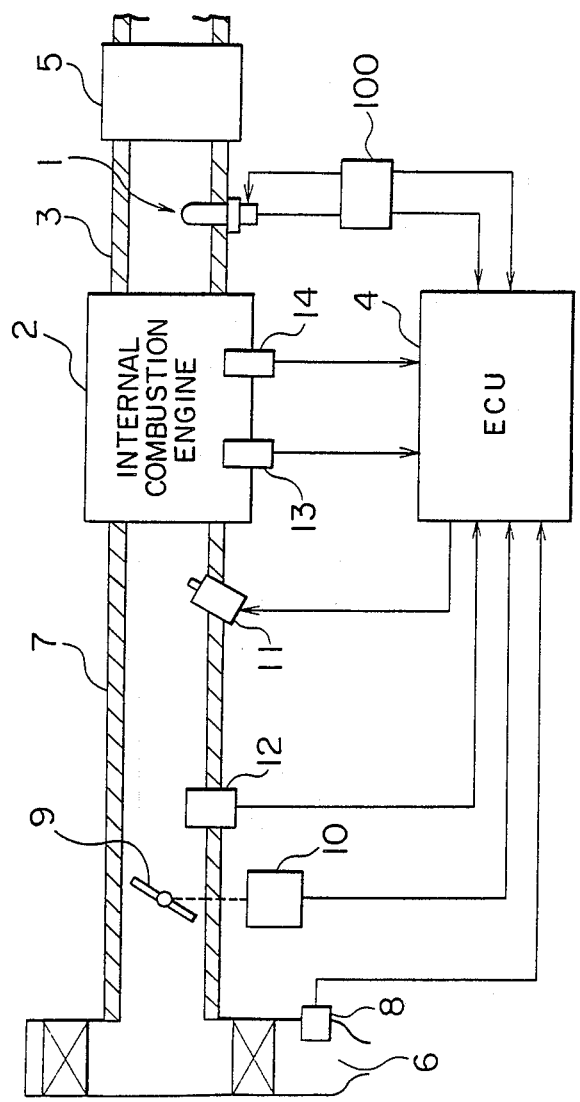
FIG. 1 is a block diagram of the overall arrangement of a fuel supply control system of an internal combustion engine, to which an oxygen concentration-sensing device according to the invention is applied.

Referring first to FIG. 1, there is illustrated the overall arrangement of a fuel supply control system for internal combustion engines, to which an oxygen concentration-sensing device according to the invention is applied. In the figure, reference numeral 1 designates an oxygen concentration (hereinafter referred to as "the $O_2$ sensor") as an exhaust concentration sensor having a heater, extending from the body of an internal combustion engine 2. In the illustrated embodiment, the $O_2$ sensor 1 is of the proportional-output type and senses the concentration of oxygen in exhaust gases emitted from the engine 2 for supplying an electrical signal indicative of the sensed oxygen concentration to an electronic control unit (hereinafter referred to as "the ECU") 4.

The $O_2$ sensor 1 is electrically connected to the ECU 4 by means of a coupler 100, hereinafter described, provided in a harness formed by electric wires.

A three-way catalyst 5 is arranged in the exhaust pipe 3 at a location downstream of the $O_2$ sensor 1 for purifying ingredients HC, CO, and NOx contained in the exhaust gases.

The engine 2 may be a four-cylinder type, for example, to which intake air is supplied through an air cleaner 6 and an intake pipe 7. An intake air temperature (TA) sensor 8 is provided in the air cleaner 6 for sensing the temperature $T_A$ of intake air and supplying an electrical signal indicative of the sense intake temperature to the ECU 4. Arranged in the intake pipe 7 is a throttle valve 9, to which is connected a throttle valve sensor 10 to supply an electrical signal indicative of the sensed opening 8TH of the throttle valve 9 to the ECU 4.

Fuel injection valves 11 are provided in the intake pipe 7 at a location downstream of the throttle valve 9 and slightly upstream of intake valves, (not shown), to supply fuel to respective corresponding cylinders of the engine 2. Each fuel injection valve 11 is connected to a fuel pump, (not shown), to be supplied with pressurized fuel therefrom, and electrically connected to the ECU 4 to have its valve opening period controlled by a driving signal therefrom.

An absolute pressure ($P_{BA}$) sensor 12 is provided in the intake pipe 7 at a location immediately downstream of the throttle valve 9 to detect absolute pressure $P_{BA}$ within the intake pipe 7. The $P_{BA}$ sensor 12 gives an electrical signal indicative of the detected absolute pressure $P_{BA}$ to the ECU 4.

An engine coolant temperature ($T_W$) sensor 13, which may be formed of a thermistor or the like, is mounted in the cylinder block of the engine 2, detects engine coolant temperature $T_W$, and supplies an electrical signal indicative of the detected engine coolant temperature to the ECU 4. An engine rotational speed ($N_e$) sensor 14 is arranged in facing relation to a camshaft, (not shown) of the engine 2 or a crankshaft of same (not shown). The $N_e$ sensor 14 is adapted to generate a pulse of a top-dead-center position (TDC) signal at one of predetermined crank angles of the engine 2, whenever the engine crankshaft rotates through 180 degrees. Pulses generated by the $N_e$ sensor 14 are supplied to the ECU 4.

Figure 2:
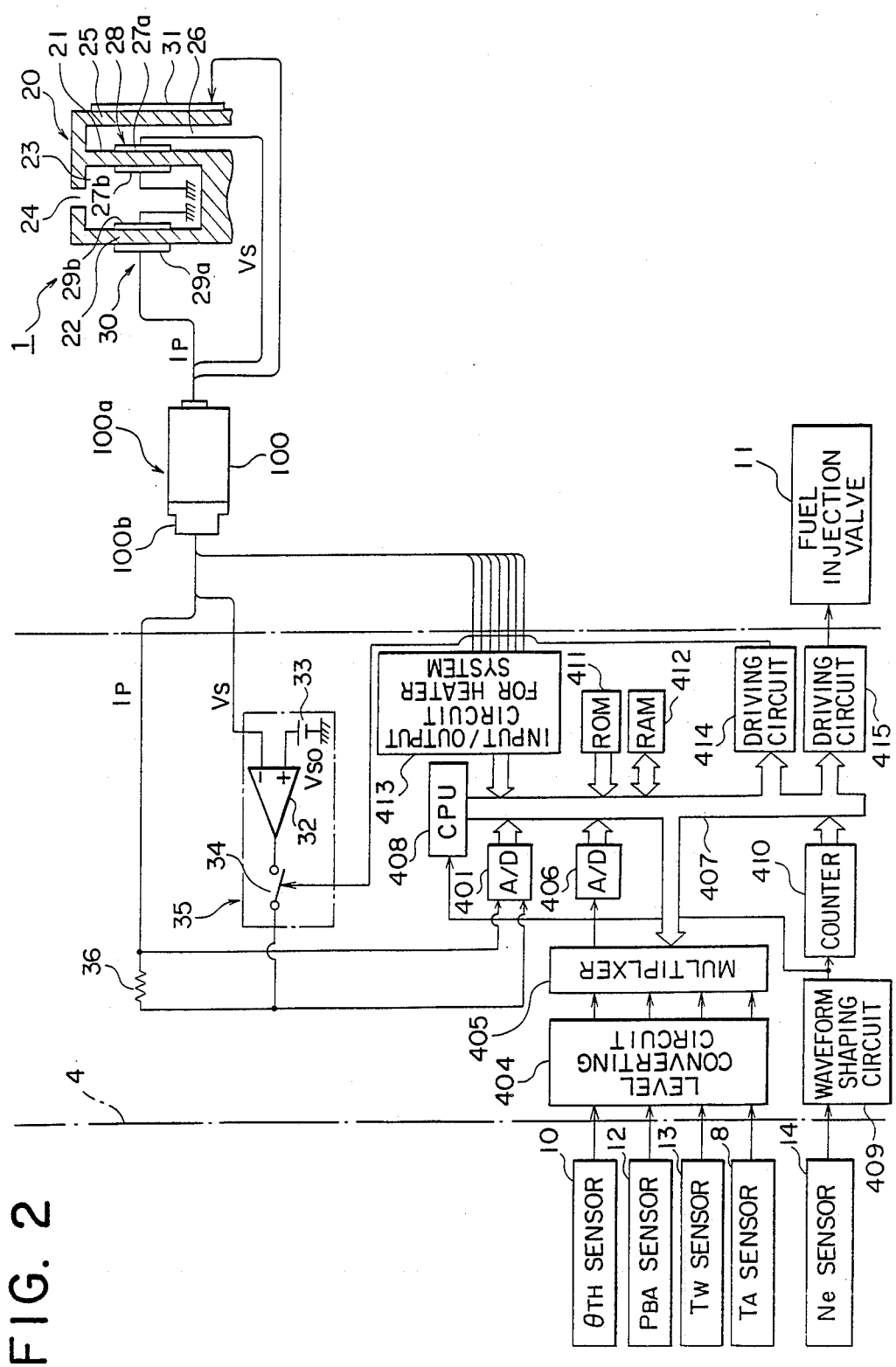
FIG. 2 is a schematic circuit diagram of the circuitry of the air-fuel ratio control system of FIG. 1, to which the oxygen concentration-sensing device according to a first embodiment of the invention is applied.

FIG. 2 shows the interior construction of the air-fuel ratio control system of FIG. 1, to which the oxygen concentration-sensing device according to a first embodiment of the invention is applied, wherein the O₂ sensor 1 as a sensor element as well as the ECU 4 in FIG. 1 are included.

The O₂ sensor 1 has a body 20 formed in a generally cubic shape and of a solid electrolytic material having oxygen ion-conductivity, such as zirconium dioxide ($ZrO_2$). the body 10 is a single element type having one cell element 28 and one oxygen-pumping element 30. Specifically, the body 20 has a first wall 21 forming part of the cell element 28 and a second wall 22 forming part of the oxygen-pumping element 30, which walls extend parallel to each other. A gas diffusion chamber 23, defined within the body 20 between the first and second walls 21 and 22, communicates with the interior of the exhaust pipe 3 through a gas-introducing slit 24 formed in the upper wall of the body 20 for introducing exhaust gases thereinto. The body 20 also has an outer wall 25 defining an air reference chamber 26 in cooperation with the first wall 21 to be supplied with air.

The first wall 21 carries on its opposite sides a couple of platinum (Pt) electrodes 27a and 27b forming part of the cell element 28, whereas the second wall 22 carries on its opposite sides a couple of platinum electrodes 29a and 29b forming part of the oxygen-pumping element 30. A heater 31 is provided on the outer surface of the outer wall 25 for heating the body 20, i.e., the cell element 28 and the oxygen-pumping element 30, for promoting the activation of the elements.

One electrode 27a of the cell element 28 on the air reference chamber 26 side is connected to an inverting input terminal of a differential amplifier 32 via the coupler 100.

On the other hand, the respective electrodes 27b and 29b of the cell element 28 and the oxygen-pumping element 30 on the gas diffusion chamber 23 side are grounded to the body 20, for example. The grounding may alternatively be carried out on the ECU 4 side, e.g., by extending lead wires from the electrodes 27b and 29b to the ECU 4 through the coupler 100.

The differential amplifier 32 forms a current-supply circuit (pumping-current supply means) 35 for supplying electric current to the O₂ sensor 1 in cooperation with a reference voltage source 33 connected to a non-inverting input terminal thereof, and a switch 34. A reference voltage $V_{so}$ from the reference voltage source 33 is set at a value, 0.4 volts, for example, which is equal to a voltage to be developed across the cell element 28 when the air-fuel ratio of a mixture supplied to the engine 2 is equal to the stoichiometric value.

The switch 34 is operated depending upon whether or not the body 20 of the O₂ sensor 1 is activated, i.e., the former is opened when the latter is in an inactivated state and closed when the latter is in an activated state. The switch 34 has one end thereof connected to one end of a current-detecting resistance 36 which has the other end connected to the electrode 29a on the outer side of the oxygen-pumping element 30. The current-supply circuit 35 and the current-detecting resistance 36 are both incorporated in the ECU 4 so that voltages at opposite ends of the resistance 36 are supplied as an output of the O₂ sensor 1 to an A/D converter of the ECU 4 for detecting the air-fuel ratio of the mixture supplied to the engine 2.

The coupler 100 connects a heater control circuit of the ECU 4 for controlling teh supply of electricity to the heater 31 so as to bring the resistance value $R_H$ of the heater 31 to a desired value. Specifically, an input-/output circuit 413 is provided in the ECU 4 for controlling the heater 31 as well as detecting the activation, i.e., temperature, of the heater 31, which is connected to the coupler 100. The input/output circuit 413 applies a voltage to the heater 31 in an ON/OFF manner and receives a signal representing the resistance value $R_H$, etc., for controlling the resistance value $R_H$ of the heater 31 to the desired value.

The coupler 100 comprises a connector 100a on the O₂ sensor 1 side, and a connector 100b on the ECU 4 side, and is adapted to accommodate resistances for compensating for variations in characteristics between individual O₂ sensors 1 used, particularly variations in resistance value $R_H$ between individual heaters 31, which occur during the manufacture thereof. The compensating resistances are more conveniently provided within the connector 100a rather than within the connector 100b, because this enables the connector 100a and the O₂ sensor 1 to be manufactured and handled as a single unit. That is, a number of units of the connector 100a and the O₂ sensor 1 are previously prepared, and have respective resistances with different resistance values corresponding to variations in characteristic of individual O₂ sensors 1, so that the variations in characteristic between the O₂ sensors used can be easily compensated for. Furthermore, many units of the connector 100a and the O₂ sensor 1 can be produced for each of the different resistance values of the compensating resistances, thereby improving the productivity of the oxygen concentration-sensing device.

When it becomes necessary to replace an O₂ sensor 1 with a new one due to failure or the like, the whole unit of the connector 100a and the O₂ sensor 1 can be replaced as a unit, thus dispensing with the necessity of repairing the connector 100b and the ECU 4 or replacing same.

On the other hand, if the compensating resistances are provided in the connector 100b on the ECU 4 side, replacement of the O₂ sensor 1 requires replacement of the entire coupler 100 including the connector 100b, thereby requiring removal of the wiring cords connecting the connector 100b and the ECU 4 and reconnection of same after replacement of the coupler 100. Particularly, if the interior of the coupler 100 is filled with resin to obtain water-proofing thereof after mounting of the compensating resistances within the coupler 100, as hereinafter referred to, it is no longer possible to replace the compensating resistances alone. This renders the provision of the compensating resistances within the connector 100a still more advantageous.

However, the present invention is not limited to the provision of the built-in resistances within the connector 100a; if required, they may alternatively be provided within the connector 100b.

Figure 5:
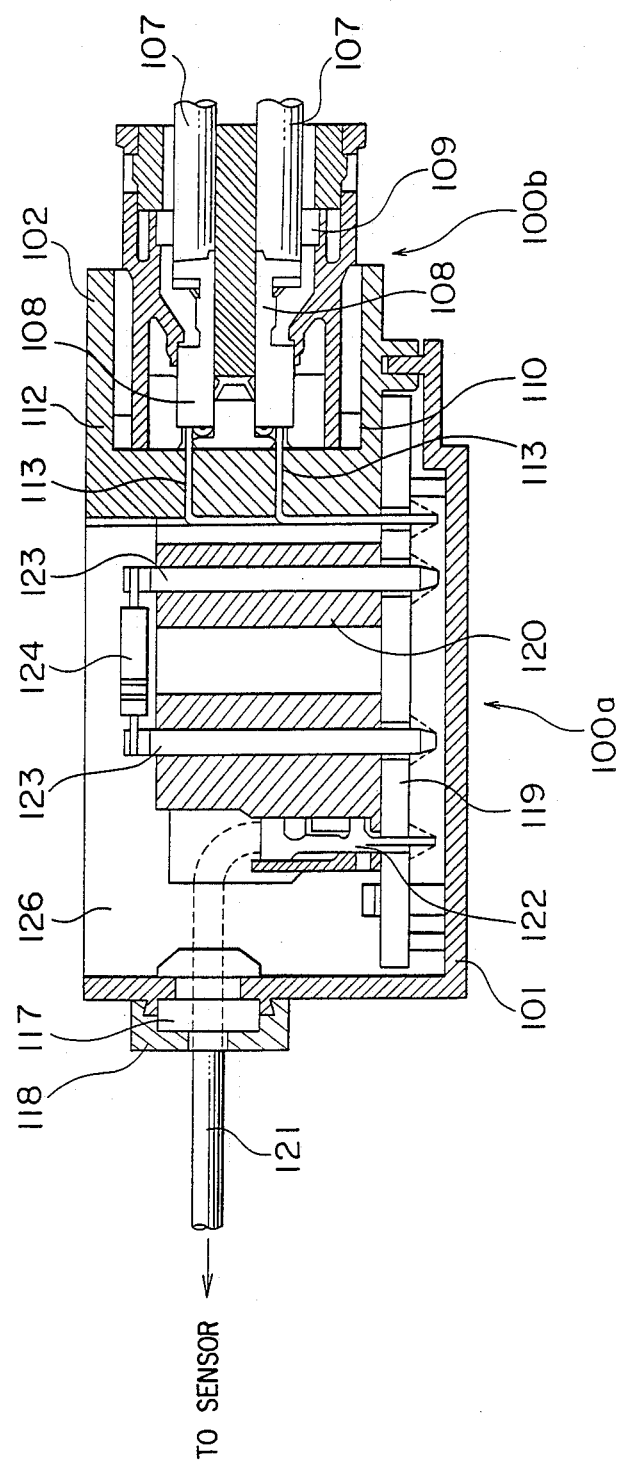
FIG. 5 is a longitudinal cross-sectional view of the coupler of FIG. 3.

FIGS. 3 through 5 show in detail the coupler 100 of the invention, wherein the coupler 100 is water-proof and is adapted to accommodate compensating resistances having different resistance values in the connector 100a thereof.

In the figures, the connector 100a comprises a casing 101 formed of resin such as polyester, and a receiving portion 1O₂ into which an inserting portion 105 of the connector 100b is removably inserted or fitted. The receiving portion 102 has a locking portion 103 formed on opposite side surfaces thereof to be firmly fitted into a front portion of the casing 101. The connector 100b comprises a casing 104 formed of resin such as polyester, and an inserting portion 105 projecting integrally from one end of the casing 104. Provided within the casing 104 is a seal-protection cap 106 formed of polyester, for example, through which a predetermined number (e.g. eleven) of, wiring cords 107 extend.

Each wiring cord 107 has one end thereof provided with a female connecting terminal 108 clamped thereon, which terminal is disposed and fixed in place within the connector 100b, as shown in FIGS. 4 and 5. A seal 109 formed of silicone rubber, for example, is disposed within the connector 100b to seal between the wiring cords 107 and the casing 104, as shown in FIG. 5. The wiring cords 107 extending from the connector 100b lead to the ECU 4 to be connected to the input/output circuit 413.

The receiving portion 1O₂ of the connector 100a has therein a seal-protection cap 111 formed of polyester, for example, for protecting a seal 110 formed of silicone rubber, for example, as shown in FIG. 3. Male connecting terminals 113 in the form of pins extend through a wafer 112 formed of polyester, for example, forming the receiving portion 102 at locations corresponding, respectively, to the female terminals 108 of the connector 100b, so that, when the both connectors 100a and 100b are mated together, electrical connection is established through the terminal pins 113 and the respective female terminals 108, as shown in FIG. 5.

The casing 101 of the connector 100a has opposite lateral side walls thereof each formed integrally with a semi-cylindrical portion 115 with a bore through which a sleeve 114 which has been galvanized, for example, is fitted, and a rear end wall thereof through which a harness 116 from the O₂ sensor 1 is connected to the connector 100a. To this end, the rear end wall of the casing 101 is mounted with a seal 117 formed of neoprene, for example, as well as a seal-supporting cap 118 formed of polyester, for example, for water-proof sealing between the harness 116 and the casing 101, as shown in FIGS. 3 and 5.

Accommodated within the connector 100a are a printed circuit board 119, and a wafer 120 formed of polyester, for example. Inner ends of the male terminals 113 are soldered to a circuit on the printed circuit board 119 for electrical connection thereto.

The wiring cords 121 of the harness 116 each have one end thereof disposed inside the connector 100a and mounted with a board-in terminal 122 soldered to the circuit on the printed circuit board 119, thereby ensuring positive connection between the cords 121 and the circuit board 119. Ends of the cords 121 of the harness 116 remote from the connector 100a are connected to the heater 31 of the O₂ sensor 1 as well as to the electrodes thereof, as shown in FIG. 3. Thus, the connector 100a and the O₂ sensor 1 are connected together, as a single unit.

A plurality pairs of cylindrical pins 123 are inserted through the wafer 120 with respective ends thereof projected from upper and lower end faces of the wafer 120. The lower ends of the cylindrical pins 123 are connected to the circuit on the printed circuit board 119 by soldering.

Resistances accommodated within the connector 100a include compensating resistances for compensating for variation in the resistance value $R_H$ between heaters 31, part of which are used to determine whether the O₂ sensor 1 is in an activated state based upon the detected resistance value $R_H$ of the heater 31. These resistances include solid resistances 124 as compensating resistances R3, R5, and R7 shown in FIG. 6, hereinafter referred to, which are soldered at their ends to the corresponding pairs of the upper ends of the cylindrical pins 123, and chip resistances R8-R11 shown in FIG. 6, also referred to later, which are secured to the circuit board 119 and connected to the circuit thereon.

As shown in FIG. 3, four solid resistances 124 are mounted onto respective four pairs of cylindrical pins 123 after assemblage of the connector 100a, as indicated by arrow 125.

One pair of the cylindrical pins 123 is used for mounting a label resistance for determining the value of an air-fuel ratio correction coefficient in response to the output of the O₂ sensor 1. O₂ sensors 1 of the proportional-output type as used in the present embodiment generally have the drawback that there may be variations in the detected air-fuel ratio between individual sensors due to variations int he diameter of the gas-introducing slit 24 produced during the manufacture of the sensors, etc. To avoid this, the resistance value of the label resistance is set at a value corresponding to the deviation of the air-fuel ratio detected by an O₂ sensor used, with reference to the resistance value of a reference O₂ sensor so that when used, it serves to eliminate the deviation.

If, when the connector 100a accommodating the label resistance is electrically connected with the connector 100b, the label resistance is automatically connected at one end thereof to an exclusive voltage source generating a predetermined voltage, 5 volts, for example, via the circuit on the circuit board 119, the male terminal 113, the female terminal 108, and the wiring cord 107, a voltage or an amount of electric current representing the deviation of the resistance value of the label resistance is inputted to the ECU 4 through the other end of the label resistance as variation correcting information. In the present embodiment, the connector 100b on the ECU 4 side also serves to apply the voltage to the label resistance and input the variation correcting information through a wiring cord and an input port. (neither of which is shown)

The remaining pairs of the cylindrical pins 123 are for mounting compensating solid resistances for controlling the heater 31, i.e., a resistance for heater high reference (HHR) signal, a resistance for heater trigger reference (HTR) signal, and a resistance for heater low reference (HLR) signal. The HHR resistance and the HLR resistance are used for setting upper and lower ranges of activation temperature of the heater 31, whereas the HTR resistance is for setting a desired middle temperature within the range.

Thus, the connector 100b serves to supply the ECU 4 with the above-mentioned signals HHR, HTR, and HLR as well as a heater base signal HBS representing the actual resistance value of the heater 31, and hence the actual temperature thereof, and to supply the heater 31 with heater power HPWR applied to the heater 31 at both ends thereof, and reference power RPWR for detecting the resistance value of the heater 31.

An internal space 126 in the connector 100a is filled with resin, after electrical connection with the harness 116 and mounting of the resistances are completed, whereby the entire coupler 100 has a water-proof structure for positively preventing corrosion of the printed circuit board 119, and improving the vibration resistance of the printed circuit board 119 and, the soldering portions.

It is desirable for the compensating resistances of the the electrical circuit of the coupler 100 to have their resistance values maintained at initially set values. However, intrusion of rain water into the coupler 100 or vibration of same may cause a change in the contact resistance of connecting points within the coupler 100, which results in deviation of the electrical characteristic of the electrical circuit. This possibility can be avoided by the resin-filled structure of the coupler 100. Thus, the coupler 100 can maintain the initial resistance values of the compensating resistances over a long time, thereby enhancing reliability and stable performance.

Further, the ECU 4 includes a level shifting circuit 404 which shifts output voltages from various sensors such as the intake air temperature ($T_A$) sensor 8, the throttle valve opening ($\theta TH$) sensor 10, the intake pipe absolute pressure ($P_{BA}$) sensor 12, and the engine coolant temperature ($T_W$) sensor 13, to a predetermined level. The level-shifted output voltages are then successively supplied to an A/D converter 406 through a multiplexer 405. The A/D converters 401 and 406 each convert the analog values of the level-shifted input signals to corresponding digital values, and supply them to a central processing unit (hereinafter referred to as "the CPU") 408 via a data bus 407.

An output signal from the engine rotational speed ($N_e$) sensor 14 has its waveform shaped by a waveform shaper 409, and the shaped signal is supplied to both the CPU 408 and a counter 410. The counter 410 counts the time interval between an immediately preceding pulse of the TDC signal and a present pulse of same, the counted value Me thereof being proportional to the reciprocal of the engine rotational speed $N_e$. The counter 410 supplies the counted value Me to the CPU 408 via the data bus 407.

Further connected to the CPU 408 via the data bus 407 are a read-only memory (hereinafter referred to as "the ROM") 411, a random access memory (hereinafter referred to as "the RAM") 412, and driving circuits 414 and 415. The RAM 412 temporarily stores results of operations executed by the CPU 408, whereas the ROM 411 stores control programs to be executed by the CPU 408 and maps or the like for calculating the fuel injection period $T_{OUT}$ of the fuel injection valves 11.

The CPU 408 is also supplied with a heater activation signal HACT, hereinafter referred to, which is generated by the input/output circuit 413. The driving circuit 414 delivers a switching signal to the switch 34 to energize and deenergize the heater 31 of the $O_2$ sensor 1 in response to the HACT signal which is received.

The CPU 408 operates in response to various engine operating parameter signals referred to above, to determine operating conditions or regions in which the engine is operating, inclusive of a feedback control region, based on a control program, (not shown) and then to calculate the fuel injection $T_{OUT}$ for which each fuel injection valve 11 should be opened in accordance with the determined operating conditions or regions of the engine 2, to thereby supply a driving signal via the driving circuit 415 to the fuel injection valve 11. In the feedback control region, the air-fuel ratio of the mixture supplied to the engine 2 is controlled to a desired value in a feedback manner responsive to the output from the $O_2$ sensor 1.

During the feedback control of the air-fuel ratio, the $O_2$ sensor 1 senses the oxygen concentration in the exhaust gases in the following manner:

When the engine 2 is operating, exhaust gas emitted from the engine 2 is introduced into the gas diffusion chamber 23 through the gas-introducing slit 24. There occurs a difference in oxygen concentration between the gas diffusion chamber 23 and the air reference chamber 26. When the cell element 28 is in an activated state, a voltage Vs is developed between the two electrodes 27a and 27b, which voltage corresponds to the difference in oxygen concentration between the chambers 23 and 26. This voltage $V_s$ is supplied to the inverting input terminal of the differential amplifier 32 via the wiring cord 121 of the harness 116, the board-in terminal 122 within the coupler 100, the circuit on the printed circuit board 119, the male terminal 113, the female terminal 118, and the wiring cord 107, as shown in FIG. 5. The reference voltage $V_{so}$ applied to the non-inverting input terminal of the differential amplifier 32 is set at such a value that it is equal to the voltage $V_s$ developed across the cell element 28 when the air-fuel ratio of the mixture is equal to the stoichiometric value, as already mentioned.

Consequently, as the air-fuel ratio of the mixture changes to the lean side, the voltage $V_s$ across the cell element 28 becomes lower than the reference voltage $V_{so}$ so that the output of the differential amplifier 32 assumes a positive level.

When the temperature of the heater 31 is within a predetermined activation temperature range with a middle value equal to a desired value, the switch 34 is closed so that the above positive-level output voltage of the differential amplifier 32 is applied to the oxygen-pumping element 30, via the closed switch 34, the current-detecting resistance 36, and the coupler 100. When the oxygen-pumping element 30 is in an activated state, the applied positive-level output voltage causes oxygen present within the gas diffusion chamber 23 to be ionized and moved through the second wall 22 to be emitted as an oxygen gas from the electrode 29a. As a result, oxygen is pumped the gas diffusion chamber 23 and pumping current Ip flows from the electrode 29a via the wall 22 to the electrode 29b.

On the other hand, as the air-fuel ratio of the mixture changes to the rich side, the voltage $V_s$ across the cell element 28 becomes higher than the reference voltage $V_{so}$ so that the output of the differential amplifier 32 assumes a negative level, oxygen present outside the O2 sensor 1 is pumped into the gas diffusion chamber 23 and pumping current Ip flows from the electrode 29b via the wall 22 to the electrode 29a in a manner inverse to that described above.

When the air-fuel ratio of the mixture is equal to the stoichiometric value, the voltage $V_s$ across the cell element 28 becomes equal to the reference voltage $V_{so}$ so that the output of the differential amplifier 32 is zero. Thus, oxygen is not pumped out of or into the gas diffusion chamber 23, and hence no pumping current IP flows.

As described above, oxygen is pumped out of and into the gas diffusion chamber 23, and hence no pumping current Ip flows.

As described above, oxygen is pumped out of and into the gas diffusion chamber 23 is performed and hence pumping current Ip flows between the electrodes 29a and 29b so as to maintain the oxygen concentration within the gas diffusion chamber 23 constant. As a result, the amount of the pumping current Ip varies in proportion to the oxygen concentration in the exhaust gases both when the air-fuel ratio of the mixture is on the lean side and when it is on the rich side. The pumping current Ip is detected from the amount of a drop in voltage across the current-detecting resistance 36 by the ECU 4, which determines the actual air-fuel ratio from the detected pumping current Ip as the output of the O2 sensor In this way, the air-fuel ratio of the mixture is detected based on the output of the O2 sensor 1, when the cell element 28 is in the activated state.

Figure 6:
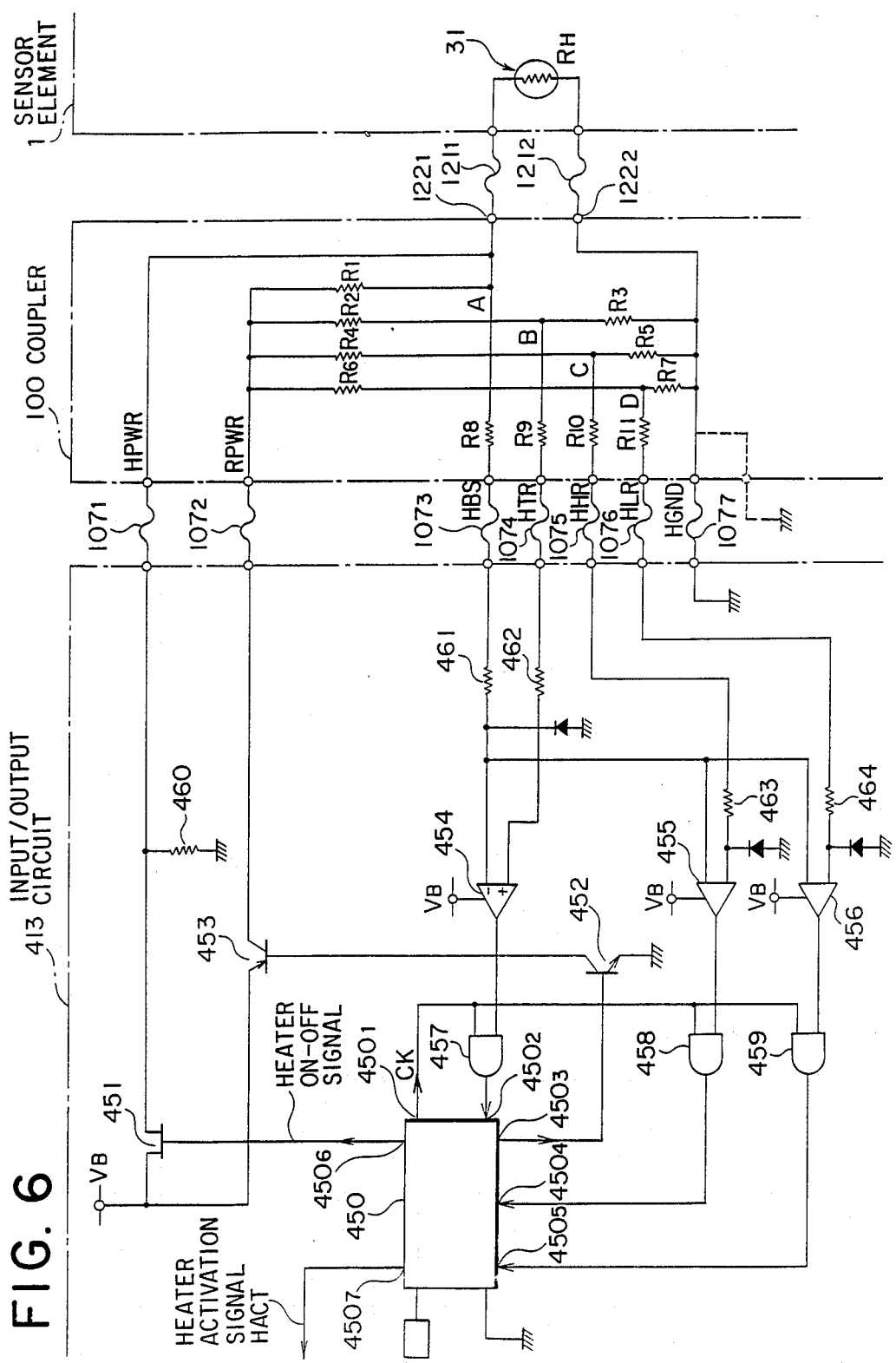
FIG. 6 is a circuit diagram of a heater control circuit in FIG. 2.

FIGS. 6 shows a control circuit for controlling the heater 31 of the device according to the first embodiment of the invention.

The control circuit comprises the input/output circuit 413 of the CPU 4, the resistances built in the coupler 100, and the heater 31 of the O2 sensor 1. The input/output circuit 413 includes a control/processing circuit 450 for generating the heater activation signal HACT, as shown in (a) of Fig. 7, a power MOSFET 451 for generating the heater power signal HPWR, as shown in (a) of FIG. 8, a first transistor 452 and a second transistor 453 for supplying the reference power signal RPWR, as shown in (b) of FIG. 8, first, second, and third differential amplifiers (operational amplifiers) 454, 455, and 456 for determining the temperature of the heater 31 from the resistance value $R_H$ of the heater 31, and first, second, and third AND gates 457, 458, and 459 which have one input terminal thereof supplied with respective outputs from the differential amplifiers 454, 455, and 456.

The control/processing circuit 450 has an output terminal $450_1$ for applying to the first, second, and third AND gates 457, 458, and 459 a clock signal CK generated at constant time intervals as a timing pulse in response to which the heater base signal HBS is supplied to the circuit 450, input terminals $450_2$, $450_4$, $450_5$ supplied with outputs from the AND gates 457, 458, 459, respectively, an output terminal 4503 for supplying a switching signal to the first and the second transistors 452 and 453 synchronously with the clock signal CK, an output terminal 4506 for supplying the heater ON-OFF signal to the MOSFET 451, as shown in (b) of FIG. 7, and an output terminal $450_7$ for supplying the heater activation signal HACT.

The MOSFET 451 has its source and drain connected to a power source VB and a wiring cord $107_1$, respectively, and its gate connected to the output terminal $450_6$ of the control/processing circuit 450. Further, a junction between one end of the wiring cord $107_1$ and the MOSFET 451 is grounded via a resistance 460 having a resistance value of 10 kilohms, for example.

The first transistor 452 has its emitter grounded, its base connected to the output terminal $450_3$ of the circuit 450 for receiving the switching signal generated synchronously with the clock signal CK therefrom. The collector of the first transistor 452 is connected to the base of the second transistor 453, which has its emitter and collector connected to the power source VB and a wiring cord $107_2$, respectively. As the first and second transistors 452, 453 are turned on and off by the signal from the output terminal $450_3$ of the control/processing circuit 450, the voltage RPWR of 10 volts, for example, is applied to the resistances within the coupler 100 via the wiring cord $107_2$ at constant time intervals.

The first differential amplifier 454 has an inverting input terminal thereof connected to a wiring cord $107_3$ via an input resistance 461 with a resistance value of 1 kilohms, for example, and the second and third differential amplifiers 455 and 456 have also one input terminal thereof connected to the wiring cord $107_3$ via the input resistance 461. The first differential amplifier 454 has a non-inverting input terminal thereof connected to a wiring cord $107_4$ via an input resistance 462 with a resistance value of 1 kilohms, for example, whereas the other input terminals of the second and third amplifiers 455, 456 are connected to wiring cords $107_5$, $107_6$ via input resistances 463, 464 both with a resistance value of 1 kilohms, for example, respectively.

Within the coupler 100, one end of the wiring cord $107_1$ connected at the other end to the FET 451 is directly connected to the board-in terminal 1221 via the circuit on the circuit board 119, as shown in FIG. 6.

The board-in terminal 1221 is connected via a wiring cord $121_1$ to one end of the heater 31 which has the other end connected via a wiring cord $121_2$ to the board-in terminal $122_2$ of the coupler 100. The board-in terminal $122_2$ is in turn connected to the input/output circuit 413 via the circuit on the circuit board 119 and a wiring cord $107_7$. In the illustrated embodiment, the wiring cord $107_7$ is grounded at a location inside the input/output circuit 413. This grounding of the heater 31 may be made to the body 20 of the O2 sensor 1, similarly to the electrodes 27b, 29b, or to the casing 101 of the coupler 100, as indicated by the broken line in FIG. 6.

Within the coupler 100, one end of the wiring cord $107_2$ is connected to respective ends of resistances $R_1$, $R_2$, $R_3$, and $R_4$ of the built-in resistances. The resistance $R_1$ with a resistance value of 5.2 kilohms, for example, is to detect the resistance value $R_H$ of the heater 31, which has the other end connected to a junction A, as shown in FIG. 6. The junction A is directly connected to the board-in terminal $122_1$, hence the heater 31 being connected to the resistance $R_1$ in series.

The junction A is also connected to the resistance $R_8$ with a resistance value of 4.0 kilohms, for example, which in turn is connected to the input/output circuit 413 via the wiring cord $107_3$ for the signal HBS.

The other respective ends of the resistance $R_2$ with a resistance value of 5.2 kilohms, for example, the resistance $R_4$ with a resistance value of 5.4 kilohms, for example, and the resistance $R_6$ with a resistance value of 5.2 kilohms, for example, are connected to one ends of the resistance $R_3$, resistance $R_5$, and resistance $R_7$. The other respective ends of the resistances $R_3$, $R_5$, and $R_7$ are connected to the board-in terminal $122_2$ to be grounded therethrough. In other words, the series circuit of the resistances $R_2$ and $R_3$, the series circuit of the resistances $R_4$ and $R_5$, and the series circuit of the resistances $R_6$ and $R_7$ are connected in parallel to the series circuit of the heater 31 and the resistance $R_1$, cooperatively forming respective bridge circuits.

In the bridge circuits thus formed, respective junctions B, C, and D, between the resistances $R_2$ and $R_3$, between the resistances $R_4$ and $R_5$, and between the resistances $R_6$ and $R_7$ are connected, respectively, to the wiring cords $107_4$, $107_5$, and $107_6$ for inputting the signal HTR, the signal HHR, and the signal HLR to the input circuit 413 via the resistance $R_9$ with a resistance value of 1.4 kilohms, for example, the resistance $R_{10}$ with a resistance value of 1.3 kilohms, and the resistance $R_{11}$ with a resistance value of 1.5 kilohms, respectively.

The compensating resistances $R_3$, $R_5$, and $R_7$ are solid resistances which are mounted on the three pairs of cylindrical pins 123, as mentioned hereinbefore. The resistance $R_3$ sets the desired or middle temperature within the activation temperature range of the $O_2$ sensor 1, the resistance $R_5$ sets the upper limit value of the activation temperature range, and the resistance $R_7$ sets the lower limit value of same. The resistance values of these resistances are set to values corresponding to the resistance value of the heater 31 used so as to compensate for variations in resistance value $R_H$ between the heaters 31 of $O_2$ sensors 1 used.

Incidentally, the resistances $R_2$, $R_4$, and $R_6$ as well as the resistances $R_8$–$R_1$ are all chip resistances.

When the reference power voltage RPWR having a given level is applied to the resistances $R_1$–$R_7$ within the coupler 100, predetermined divided voltages are developed at the junctions B, C, and D which correspond to the resistance values of the respective series circuits, respectively, whereas, at the junction A, a divided voltage having a level determined by the resistance value $R_H$ of the heater 31, i.e., a voltage representing the temperature of the heater 31, is developed. These divided voltages are, therefore, used to determine, by the use of the differential amplifiers 454, 455, and 456, whether or not the temperature of the heater 31 is higher than the desired temperature, whether or not the same temperature is above the upper limit value of the activation temperature range or not, and whether the same temperature is below the lower limit value of the same range or not, respectively, as shown in (d) of FIG. 7.

According to the first embodiment of the invention, since the compensating resistances within the coupler 100 comprise the resistances $R_3$, $R_5$, and $R_7$ for setting the desired temperature, the upper limit value, and the lower limit value, it is possible to completely correct variations in resistance value $R_H$ between the individual heaters 31 of $O_2$ sensors used and hence ensure reliable control of the $O_2$ sensor 1.

Particularly, even when the temperature of the heater 31 varies nonlinearly with respect to the resistance value $R_H$ of same, the oxygen concentration-sensing device of the first embodiment can properly control the temperature of the heater 31, by virtue of the provision of the resistances $R_5$, $R_7$ for setting the upper and lower limit values.

Further, the output of the $O_2$ sensor 1 can be stabilized by effecting the duty control of the temperature of the heater 31 to the desired temperature, even if the $O_2$ sensor 1 is of the proportional-output type in which the pumping current Ip and hence the detected air-fuel ratio tend to be largely affected by the temperature of the heater 31.

In the heater control circuit of FIG. 6, if the desired temperature is 700° C., the upper limit value is 800° C., and the lower limit value is 700° C., the relationship between the temperature of the heater 31, the resistance value $R_H$ of same, and the voltage to be applied to same may be set as below:

800° C./5.625 ohms/6.2356 volts
(2.356 millivolts/° C.)
700° C./5.2 ohm/6.0 volts
(4.25 millivolts/° C.)
600° C./4.775 ohms/5.7444 volts
(2.55 millivolts/° C.) wherein the resistances $R_3$, $R_5$, and $R_7$ have set values of 5.2 kilohms, 5.625 kilohms, and 4.775 kilohms, respectively.

With the above described arrangement of the heater control circuit, the heater power HPWR is supplied from the input/output circuit 413 to the heater 31, as shown in (b) of FIG. 7. In FIG. 7, during time periods $t_{10}$–$t_{12}$ and $t_{14}$–$t_{15}$, the heater ON-OFF signal HPWR is controlled by the control/processing circuit 450 to go high at predetermined time intervals of 16.384 milliseconds, for example, to remain high for a time period $\tau_{ON}$, and to turn off and remains off for a time period $\tau$—$\tau_{ON}$ (256 microseconds, for example). That is, the high-level voltage HPWR is applied to the heater 31 during the time period $\tau_{ON}$. On the other hand, during the time period $\tau$—$\tau_{ON}$ the reference power voltage RPWR is applied to the compensating resistances. Since the voltage RPWR is supplied synchronously with the clock signal CK, it is applied to the compensating resistances even when the heater power HPWR is not generated, e.g., during time period $t_{12}$–$t_{14}$ shown in (b) of FIG. 7.

FIG. 8 shows the relationship in timing between turning-off of the voltage HPWR, turning-on of the signal voltage RPWR, and the clock signal CK. The voltage RPWR is applied to the compensating resistances for a predetermined time period $T_2+T_3$ ($T_1=T_2+T_3$) while the voltage HPWR is off for a time period of $T_1$ ($t_1=\tau-\tau_{ON}$), as shown in (a) and (b) of FIG. 8. The clock signal CK is generated at the end of the time period T2, as shown in (c) of Fig. 8.

The reason for setting the timing of generation of the voltages HPWR and RPWR, and the signal CK as above is as follows:

The temperature of the heater 31 is controlled by duty control, i.e., by, turning on and turning off the voltage HPWR, wherein when the time period of turning-off of the voltage HPWR is 256 microseconds as the maximum duty ratio is 97%. However, the voltage HPWR is turned on and turned off by the MOSFET 451 with some time lag in turning from ON to OFF. Also, the transistor 453 which controls the voltage RPWR has some time lag in turning from OFF to ON. However, to detect the resistance value $R_H$ of the heater 31 stably and accurately, the ON or OFF time period of the voltage HPWR and the OFF or ON time period of the voltage RPWR should not overlap each other (if these time periods overlap, a voltage representing the temperature of the heater 31 can vary). In addition, the clock signal CK has to be generated during turning-off of the voltage RPWR at a time point when the voltage RPWR has become stabilized.

Therefore, the time period $T_2$ is provided as the front portion of the whole ON time period of the voltage RPWR, as shown in (b) of FIG. 8 so that the heater base level HBS representing the resistance value $R_H$ of the heater 31 is latched by the clock signal CK, thereby stably and accurately detecting the resistance value $R_H$ of the heater 31. The time period $T_2$ is set at 192 microseconds, for example, taking into consideration the time lag of turning-off of the MOSFET 451, the time lag of turning-on of the transistor 453, and the time period in which the voltage of the bridge circuits of the coupler 100 becomes stable after the voltage RPWR is applied thereto. The time period $T_3$ is set at 64 microseconds, for example, which is the minimum value of the clock signal CK pulse width.

If the voltage RPWR and the clock signal CK are generated at the above-mentioned timing, when the voltage RPWR is applied to the compensating resistances of the coupler 100, a voltage corresponding to the temperature of the heater 31 is developed at the junction A during a time period $t_{10}-t_{16}$ shown in (d) of FIG. 7, which is supplied to the input/output circuit 413 as the signal HBS representing the temperature of the heater 31. At the same time, a divided voltage having a predetermined level is developed at the junction B, which is supplied as the heater trigger reference signal HTR to the circuit 413. The signal HBS represents the actual temperature, i.e., the actual resistance value $R_H$, of the heater 31, whereas the signal HTR represents a resistance value corresponding to the desired temperature of the heater 31. The signals HBS and HTR are supplied to the first differential amplifier 454, where their levels are compared with each other, and the first AND gate 457 is supplied with an output signal from the differential amplifier 454, which represents whether or not the actual temperature of the heater 31 is higher or lower than the desired temperature. Since the clock signal CK is now applied to the AND gate 457, the output from the differential amplifier 454 is supplied through the AND gate 457 to the control/processing circuit 450. Thus, the heater ON-OFF signal is generated by the control/processing circuit 450 based upon the comparison result from the differential amplifier 454, to cause the MOFFET 451 to be turned on and off to control the supply of voltage HPWR, with a duty ratio corresponding to the comparison result.

In the timing chart of FIG. 7, the voltage HPWR is turned on at time points $t_{10}$, $t_{11}$, $t_{14}$, and $t_{15}$ when the detected heater temperature is below the desired temperature, whereas it is turned off at time points $t_{12}$, $t_{13}$, and $t_{16}$ when the former is above the latter.

When the voltage HPWR is supplied, a determination is made as to whether or not the $O_2$ sensor 1 is in an activated state, as described below.

When the voltage RPWR is applied to the resistances of the coupler 100, predetermined divided voltages are developed at the junctions C and D by means of the resistances $R_4$, $R_5$ and the resistances $R_6$, $R_7$, which are applied to the second and third differential amplifiers 455 and 456, as a high reference signal HHR and a low reference signal HLR, respectively. These differential amplifiers 455, 456 are each also supplied with the heater base voltage HBS. The signals HHR and HLR represent the upper limit value and lower limit value of the activation temperature range, respectively. The second and third differential amplifier 455, 456 compare these signals HHR and HLR with the signal HBS to output a signal representing that the actual heater temperature is above the upper limit value, and a signal representing that the former is below the lower limit value, respectively. The respective outputs are supplied to the control/processing circuit 450 through the respective AND gates 458 and 459. The signals thus supplied to the circuit 450 represent the actual state of activation of the heater 31 or the $O_2$ sensor 1. The circuit 450 outputs the heater activation signal HACT indicative of whether the $O_2$ sensor is activated or inactivated from the output terminal $450_7$ thereof.

Specifically, according to the example of FIG. 7, the detected heater temperature, is below the lower limit value at a time point $t_{10}$, and hence it is determined that the $O_2$ sensor 1 is in an inactivated state. Then the signal HACT is outputted at a low level. Thus, it is determined that the $O_2$ sensor 1 is in an activated state, from the resistance value $R_H$ of the heater 31. Further, the activation state of the $O_2$ sensor 1 can be easily and accurately determined merely by applying the voltage RPWR to the resistances of the coupler 100 and detecting the voltages developed at the predetermined junctions, even when the voltage HPWR is not applied.

At the time point $t_{13}$ in FIG. 7, the heater temperature is above the higher limit value, and hence it is determined that the $O_2$ sensor 1 is at a high temperature. Then, the signal HACT is generated at a low level representing a high-temperature inactivated state, because excessive energization of the heater 31 is to be avoided.

As described above, when the temperature of the heater 31 is above the upper limit value or below the lower limit value, and hence the $O_2$ sensor 1 is out of the activation temperature range, the heater activation signal HACT is outputted at a low level from the control/processing circuit 450, whereas, when the temperature of the $O_2$ sensor 1 is within the activation temperature range, e.g., at the time points $t_{11}$, $t_{12}$, $t_{14}-t_{16}$ in FIG. 7, the HACT signal is outputted high level.

The signal HACT thus formed is used to energize and deenergize the oxygen-pumping element 30 of the $O_2$ sensor 1. To be specific, when the resistance value $R_H$ shows that the heater 31 is within the activation temperature range, i.e., above the lower limit value and below the upper limit value, the CPU 408 operates in response to the signal HACT to give a command to the driving 414 to cause the switch 34 to be closed so t the pumping current Ip can flow through the oxygen-pumping element 30. By thus controlling the supply of pumping current Ip only during activation of the $O_2$ sensor, the $O_2$ sensor 1 can be protected from being excessively energized when it is at a low temperature or at a high temperature, and hence from being blackened. Further, this ensures that control of the air-fuel ratio is carried out only when the $O_2$ sensor 1 stably produces output, thereby enabling accurate detection of the oxygen concentration in the exhaust gases.

In addition, the heater control circuit shown in FIG. 6 is capable of accurately detecting the temperature of the heater 31, thereby ensuring positive determination of the activation of the $O_2$ sensor 1 even when the $O_2$ sensor 1 has again become inactivated after it has once become activated, due to lowering of the temperature of the $O_2$ sensor body 20, e.g., after long operation of the engine under low load wherein the temperature of the exhaust gases diminishes.

The $O_2$ sensor applicable to the invention is not limited to the proportional-output type. Further, the proportional-output type is not limited to a single element type as in the illustrated, but may be a dual element type.

Figure 9:
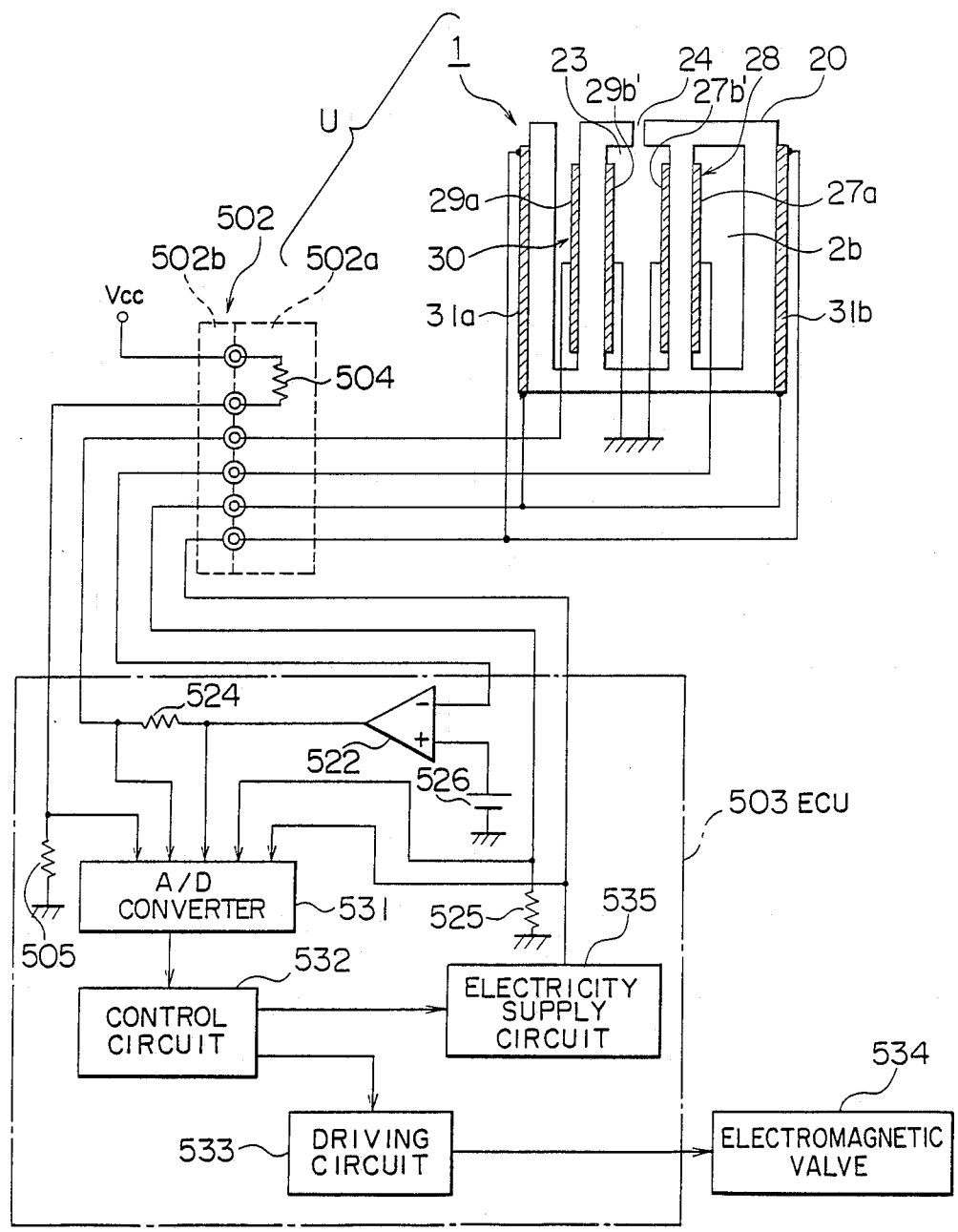
FIG. 9 is a circuit diagram of an oxygen concentration-sensing device according to a second embodiment of the invention.
Figure 10:
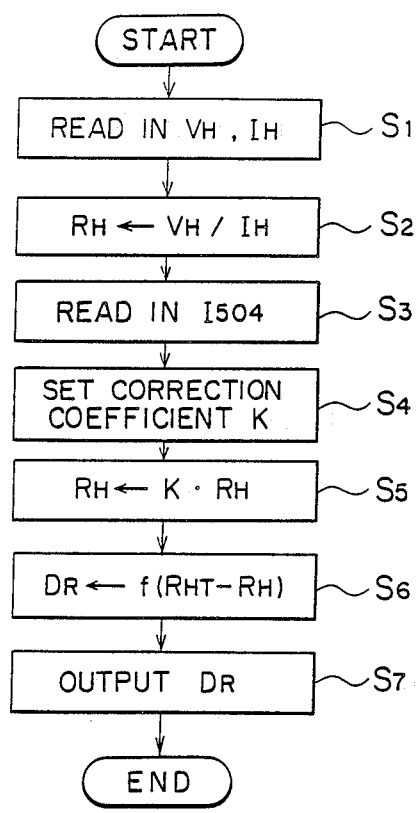
FIG. 10 is a flow chart of a program which is executed in the device of FIG. 9.

FIGS. 9 through 10 show a second embodiment of the invention. The oxygen concentration-sensing device of the second embodiment is different from the device of the first embodiment described above, in that a coupler 502 has a single compensating resistance 504 in place of a plurality of resistances forming bridge circuits together with the heater 31.

In FIGS. 9 and 10, like reference numerals designate elements and parts similar to those in Figs. 3 through 8, and description thereof is omitted.

An $O_2$ sensor 1 is connected to an ECU 503 through a coupler 502, which is composed of a connector 502$_a$ on the $O_2$ sensor 1 side, and a connector 503 on the ECU 503 side, similarly to the first embodiment. The connector 502$_a$ and the $O_2$ sensor 1 cooperate to form a detecting unit U. The connector 502$_a$ has a resistance 504, hereinafter described, incorporated therein.

The ECU 503 comprises a differential amplifier 522, a resistance 524 for detecting electric current flowing through an oxygen-pumping element 30, a resistance 525 for detecting electric current flowing to a heater 31, a reference voltage source 526, an A/D converter 531, a control circuit 532, a driving circuit 533, and a heater-power supply circuit 535, as shown in FIG. 9. The outer electrode 29$a$ of the oxygen-pumping element 30 is connected to an output terminal of the differential amplifier 522 through the resistance 524, whereas the inner electrode 27$b$ of same is grounded. The outer electrode 27$a$ of the cell element 28 is connected to an inverting input terminal of the differential amplifier 522, whereas the inner electrode 27$b$ of same is grounded. The reference voltage source 526 is connected to a non-inverting input terminal of the differential amplifier 522. The reference voltage source 526 has an output voltage thereof set at a value which is equal to a voltage developed across the cell element 28 when the air-fuel ratio of the mixture is equal to the stoichiometric value. The output of the $O_2$ sensor 1 is detected in terms of a voltage across the resistance 524, i.e., a difference in potential between opposite ends of the resistance 524, which is supplied to the control circuit 532 through the A/D converter 531, and read into the control circuit 532, as representing the pumping current Ip flowing through the oxygen-pumping element 30.

The control circuit 532 comprises a microcomputer, to which are connected various engine parameter sensors, (not shown), such as an engine rotational speed ($N_e$) sensor, an intake absolute pressure ($P_{BA}$) sensor, and an engine coolant temperature ($T_W$) sensor. An electromagnetic valve 534 is connected to the control circuit 532 through the driving circuit 533, and arranged in a secondary air supply passage, (not shown), communicating with an intake manifold, (not shown), of the engine 2 at a location downstream of a throttle valve, (not shown).

The heater 31 composed of heater elements 31$a$, 31$b$ is supplied with electric current from the heater power-supply circuit 535 to be heated to heat the oxygen-pumping element 30 and the cell element 28 to an appropriate temperature higher than the temperature of exhaust gases. The heater power-supply circuit 535 is supplied with a control signal indicative of a duty ratio from the control circuit 532 to control the electric current flowing to the heater 31 based on the duty ratio, so that the temperature of the heater 31 becomes equal to a desired value. The control circuit 532 is also supplied with a volta VH developed between opposite end terminals of the heater 31 picked up by the resistance 525 via the A/D converter 531 so that the voltage (heater voltage) VH is read into the control circuit 532, as representing an amount of electric current IH flowing through the heater 31.

The compensating resistance 504 as a circuit element having a circuit constant corresponding to the temperature vs. current characteristic of the heater 31 used, i.e., the resistance value $R_H$ thereof, is incorporated in the connector 502$a$ on the $O_2$ sensor 1 side. A constant voltage Vcc from a constant-voltage regulated power supply, (not shown) is applied to the compensating resistance 504, so that a voltage at the junction between the compensating resistance 504 and a resistance 505 serially connected thereto is inputted to the control circuit 532 through the A/D converter 531, as information representing an amount of current $I_{504}$ flowing through the heater 31, i.e., the temperature vs. current characteristic of the heater 31.

FIG. 10 shows a program for operating the control circuit 532.

First, the control circuit 532 reads in the information on the heater volta $V_H$ and the heater current $I_H$ at a step $S_1$, and then calculates the resistance value $R_H$ of the heater 31 from the values $V_H$, $I_H$ at a step $S_2$. Then the control circuit 532 reads in the information on the amount of electric current $I_{504}$ flowing through the compensating resistance 504 as representing the temperature vs. current characteristic of the heater 31, at a step $S_3$. A correction coefficient K is set by retrieving a map, hereinafter referred to, based on the current value $I_{504}$, at a step $S_4$. At a step $S_5$, the resistance value $R_H$ obtained at the step $S_2$ is multiplied by the correction coefficient K to determine a corrected value $R_H$ thereof. At the next step $S_6$, a duty ratio $D_R$ is determined from the difference between the target resistance value $R_H$T which corresponds to a desired temperature of a reference heater which has a reference temperature vs. current characteristic, and the resistance value $R_H$ obtained at the step $S_5$. The control circuit 532 then supplies the heater power-supply circuit 535 with the determined duty ratio $D_R$, at a step $S_7$.

In the manufacture of the O2 sensor 1, the compensating resistance 504 is selected from among previously prepared ones, in the following manner: First, in each of $O_2$ sensors 1 prepared, the resistance value $R_H$ of the heater 1 assumed at a predetermined temperature thereof is measured. The difference between the resistance value $R_{HS}$ of the reference heater assumed at the above predetermined temperature and the measured resistance value $R_H$, $R_{HS}-R_H$, is determined. The difference values ($R_{HS}-R_H$) thus determined are classified into an N number of classes. An N number of resistance values $R_L-R_{LN}$ are set, which correspond, respectively, to the N number of classes. Further, an N number of values $K_l-K_N$ of the correction coefficient K are set, which correspond, respectively, to the N number of the coefficient values $K_l$-KN. The above-mentioned map of R and K vs. ($R_{HS}-R_H$) is thus prepared. Then, a resistance 504 is selected from the map, which has a resistance value $R_L$ corresponding to the difference value $R_{HS}$-$R_H$ of the heater 31 of each $O_2$ sensor prepared.

The individual resistance values $R_L$-$R_{LN}$ of the map are set at standard values according to JIS (Japan Industrial Standard) or any other standards. Therefore, it is possible to use commercially available resistances with standard resistance values, making it unnecessary to use custom-made resistances with special resistance values.

The heater power-supply circuit 535 operates in response to the duty ratio signal from the control circuit 532 to control the amount of current supplied to the heater 31 to the desired value. Specifically, if, at a predetermined temperature, the heater 31 has a resistance value higher than that of the reference resistance, it is supplied with a smaller amount of current than the amount of current to be supplied to the reference resistance, whereas if, at the predetermined temperature, the heater 31 has a resistance value lower than that of the reference resistance, it is supplied with a larger amount of current than the amount of current to be supplied to the reference resistance, thereby properly maintaining the temperature of the heater 31 at the desired value.

Although, in the flowchart of FIG. 9, to determine the duty ratio $D_R$ the resistance value $R_H$ of the heater 31 is determined and the determined value $R_H$ is corrected by the coefficient K, alternatively the desired resistance value $R_{HT}$ may be corrected by a correction coefficient K'. Further, the duty ratio $D_R$ may be determined from the amount of current $I_H$ through the heater 31 and the desired amount of current $I_{HT}$ through the reference heater in place of determining the resistance value $R_H$.

Figure 11:
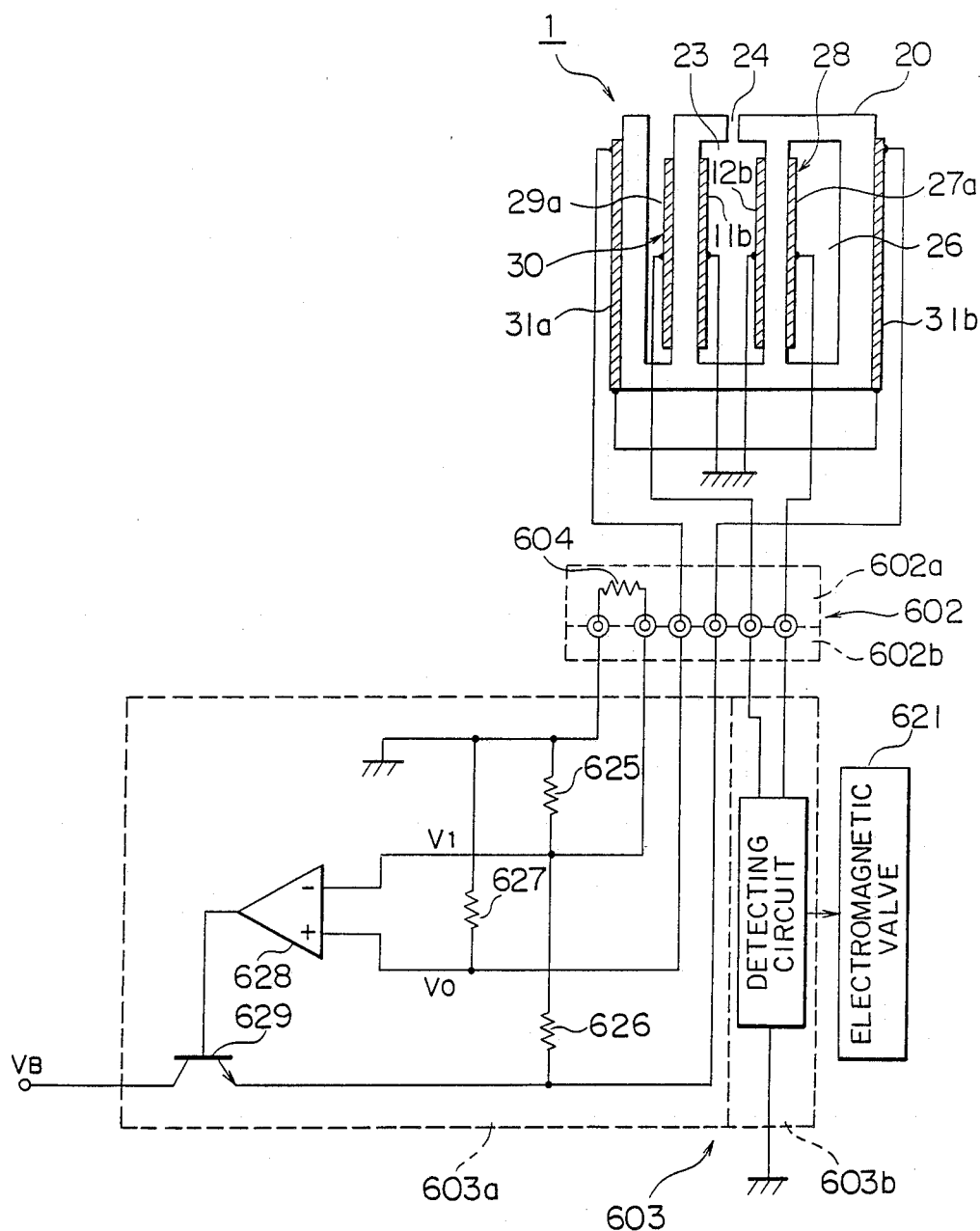
FIG. 11 is a circuit diagram of an oxygen concentration-sensing device according to a third embodiment of the invention.

FIG. 11 shows a third embodiment of the invention. The embodiment differs from the second embodiment in that a compensating resistance 604 of a coupler 602 forms part of a bridge circuit and is connected to a differential amplifier or comparator 628 of the bridge circuit, in place of being connected to the control circuit 532 through the A/D converter 531 in FIG. 10.

In FIG. 11, like reference numerals designate elements and parts similar to those in FIGS. 3 to 10, and description thereof is omitted.

An $O_2$ sensor 1 is connected to an ECU 603 through a coupler 6$O_2$, similarly to the second embodiment.

The ECU 603 comprises a temperature control circuit 603a for controlling the amount of electric current supplied to the $0_2$ sensor 1 and hence the temperature of a heater 31 composed of serially connected heater elements 31a and 31b to a desired value, and an oxygen concentration-detecting circuit 603b for detecting the output of the $O_2$ sensor 1. The oxygen concentration-detecting circuit 603b supplies an electromagnetic valve 621 provided in a secondary air supply passage of an engine (not shown) in a manner similar to the electromagnetic valve 534 in FIG. 9, with a driving signal representing the oxygen concentration of exhaust gases, whereby the electromagnetic valve 621 operates in response to the driving signal to regulate the amount of secondary air through the passage to control the air-fuel ratio of the mixture supplied to the engine 2. The temperature control circuit 603a comprises three resistances 625, 626, and 627 forming a bridge circuit in cooperation with the heater 31, the comparator 628, and a transistor 629 as a switching power amplifier. The resistance 627 is serially connected to the heater 31, while the resistances 625 and 626 are serially connected to each other. The series circuit of the resistance 627 and the heater 31 is connected in parallel to the series circuit of the resistances 625 and 626. A predetermined level of voltage VB is applied to the two series circuits 627, 31; 625, 626 through the collector and emitter of the transistor 629. A divided voltage $V_o$ at the junction between the heater 31 and the resistance 627 as well as a divided voltage $V_1$ at the junction between reference resistances 625 and 626 are supplied to respective input terminals of the comparator 628 so that the comparator 628 supplies an output signal depending on the difference between the two input voltages to the base of the transistor 629. In the embodiment, the compensating resistances 624 with a resistance value corresponding to the temperature vs. current characteristic of the heater 31 is connected in parallel to the resistance 625 and arranged within the connector 6$O_2$ a. Thus, the divided voltage $V_1$ is virtually determined by the resistances 625, 626 and the compensating resistance 604.

With the above arrangement, when the temperature of the $0_2$ sensor 1 and hence the temperature of the heater 31 lowers so that the resistance value $R_H$ of the heater 31 decreases below a predetermined value, the divided voltage $V_o$ increases above the divided voltage $V_1$. Accordingly, the output of the comparator 628 goes high to turn the transistor 629 on, whereby the predetermined level of voltage VB is applied to the series circuit of the heater 31 and the resistance 627 to energize and heat the heater 31, thereby raising the temperature of the $O_2$ sensor 1.

On the other hand, when the temperature of the heater 31 increases with an increase in the temperature of the $O_2$ sensor 1 so that the resistance value $R_H$ of the heater 31 increases above a predetermined value, the divided voltage $V_o$ decreases below the divided voltage $V_1$, whereby the output level of the comparator 628 goes low to turn the transistor 629 off to deenergize the heater 31, thereby lowering the temperature of the $O_2$ sensor 1.

The above operation is repeated so that the resistance value $R_H$ of the heater 31 is controlled to a predetermined value and hence the temperature of the heater 31 is controlled to the desired value.

As will be understood from the above, the comparator 628 and the transistor 629 cooperatively control the supply of current to the heater 31, and in this sense serve to keep the potential balance of the bridge circuit.

The compensating resistance 604, which should have a resistance value $R_L$ corresponding to the temperature vs. current characteristic of the heater 31, is selected as follows. First, in each of $O_2$ sensors 1 prepared, the resistance value $R_H$ of the heater 31 assumed at a predetermined temperature thereof is measured. The difference $R_{HS}$-$R_H$ is measured between the resistance value $R_{HS}$ of a reference heater, which was used as a criterion for determining the resistance values of the resistances 625, 626, and 627, assumed at the above predetermined temperature and the measured resistance value $R_H$ A compensating resistance 604 is selected, which corresponds to the difference value ($R_{HS}$-R thus determined. Since the compensating resistance 604 is connected in parallel to the resistance 625, the resistance value of the compensating resistance 604 thus selected determines the resultant resistance value of the compensating resistance 604 and the resistance 625. Further, the respective resistances 625 to 627 have their resistance values set such that the potential balance of the bridge circuit is established at the desired heater temperature (desired resistance value) of the reference heater to which the heater temperature (resistance value) is to be controlled. Therefore, as the comparator 628 and the transistor 629 operate so as to keep the potential balance of the bridge circuit, the heater 31 is supplied with a smaller amount of current than the amount of current to be supplied to the reference heater if the heater 31 has a resistance value higher than that of the reference heater at a predetermined temperature, whereas, when the heater 31 has a resistance value lower than that of the reference heater at the predetermined temperature, it is supplied with a larger amount of current than the amount of current to be supplied to the reference heater, thereby properly maintaining the temperature of the heater 31 at the desired value.

According to the third embodiment of the invention, the resultant resistance value of the parallel-connected resistances 604, 625 can be set by selecting the compensating resistance 604. Therefore, it suffices to previously prepare compensating resistances with larger differences in resistance value therebetween with respect to the difference value ($R_{HS}-R_H$), thereby enabling ready procurement of commercially available resistances with resistance values according to JIS or any other standards.

Although, in the illustrated embodiment, the compensating resistance 604 is connected in parallel with the resistance 625, alternatively it may be connected in parallel with the resistance 626 or 627.

What is claimed is:

1. In an oxygen concentration-sensing device including an oxygen concentration-sensing element for sensing the concentration of oxygen contained in a gas, a heater for heating said element, supply means for supplying said heater with current for heating same, control mean electrically connected to said heater for controlling the operation of said supply means so as to bring the temperature of said heater to a desired temperature, and a coupler connecting said oxygen concentration-sensing element and said control means, the improvement comprising a compensating resistance accommodated in said couplex and having a resistance value corresponding to a resistance value of said heater assumed at said desired temperature, and wherein said control means detects a resistance value of said heater only while said supply means is not operating, and then said control means controls the operation of said supply means based upon said detected resistance value of said heater and electrical information obtained from said compensating resistance.

2. An oxygen concentration-sensing device as claimed in claim 1, wherein said coupler comprises a first connector connectible to said oxygen concentration-sensing element, and a second connector disconnectably mated with said first connector connectible to said control means, said compensating resistance being accommodated within said first connector.

3. An oxygen concentration-sensing device as claimed in claim 1, including resin filled within said coupler in which said correcting resistance is buried.

4. An oxygen concentration-sensing device as claimed in claim 1, wherein said compensating resistance and said heater cooperate to form part of a bridge circuit, said control means controlling the operation of said supply means depending upon a reference voltage created by said compensating resistance and a voltage created by said heater.

5. In an oxygen concentration-sensing device including an oxygen concentration-sensing element for sensing the concentration of oxygen contained in a gas, a heater for heating said element, control means electrically connected to said heater for controlling the supply of a electrically to said heater so as to bring the temperature of said heater to a desired temperature, and a coupler connecting said oxygen concentration-sensing element and said control means, the improvement comprising a compensating resistance accommodated in said coupler and having a resistance value corresponding to a resistance value of said heater assumed at said desired temperature, and wherein said compensating resistance and said heater cooperate to form part of a bridge circuit, said control means controlling the supply of electricity to said heater depending upon a reference voltage created by said compensating resistance and a voltage created by said heater, and further including a second compensating resistance having a resistance value corresponding to a resistance value assumed by said heater when the temperature of said heater is at an upper limit of a predetermined activation temperature range, and a third compensating resistance having a resistance value corresponding to a resistance value assumed by said heater when the temperature of said heater is at a lower limit of said range, said second and third resistances forming part of a second bridge circuit and part of a third bridge circuit, respectively, in cooperation with said heater, and wherein said control means controls the supply of electricity to said heater depending upon respective second and third reference voltages created by said second and third compensating resistances, and said voltage created by said heater, in a manner such that the temperature of said heater is maintained within said activation temperature range.

6. In an oxygen concentration-sensing device including an oxygen concentration-sensing element for sensing the concentration of oxygen contained in a gas, a heater for heating said element, control means electrically connected to said heater for controlling the supply of electricity to said heater so as to bring the temperature of said heater to a desired temperature, and a coupler connecting said oxygen concentration-sensing element and said control means, the improvement comprising a compensating resistance accommodated in said coupler and having a resistance value corresponding to a resistance value of said heater assumed at said desired temperature, and means for applying a given level of voltage to said compensating resistance, and wherein said control means comprises means for supplying electricity to said heater, means for reading in electrical information obtained from said compensating resistance when said given level of voltage is applied thereto, and electrical information obtained from said heater when supplied with said electricity, as first data and second data, respectively, means for correcting said second data by said first data, and means for determining the amount of electricity to be supplied to said heater from said second data so corrected.

7. In an oxygen concentration-sensing device including an oxygen concentration-sensing element for sensing the concentration of oxygen contained in a gas, a heater for heating said element, control means electrically connected to said heater for controlling the supply of electricity to said heater so as to bring the temperature of said heater to a desired temperature, and a coupler connecting said oxygen concentration-sensing element and said control means, the improvement comprising a compensating resistance accommodated in said coupler and having a resistance value corresponding to a resistance value of said heater assumed at said desired temperature, a second resistance serially connected to said compensating resistance, and means for applying a given level of voltage to said compensating resistance and said second resistance, and wherein said control means comprises mans for supplying electricity to said heater, means for reading in information on a voltage developed at a junction between said compensating resistance and said second resistance when said given level of voltage is applied thereto, and an amount of current flowing through said heater and a voltage developed across said heater when supplied with said electricity, as first data and second data, respectively, means for calculating a resistance value of said heater from said second data so read in, means for correcting one of said resistance value calculated and a reference resistance value assumed by said heater at said desired temperature by said first data so read in, and means for determining a duty ratio corresponding to a difference between said corrected one of said resistance value calculated and said reference resistance value, and the other of same, and wherein said means for supplying electricity to said heater supplies electricity to said heater in an amount determined by said duty ratio so determined.

8. An oxygen concentration-sensing device as claimed in claim 7, wherein said control means has a map comprising a plurality of resistance values corresponding respectively to a plurality of predetermined differences between a plurality of predetermined resistance values which can be assumed by said heater at a predetermined temperature and a resistance value assumed by a reference heater at said predetermined temperature, and a plurality of correction values corresponding respectively to said plurality of resistance values, a resistance having a resistance vlaue corresponding to a difference between an actual resistance value of said heater at said predetermined temperature and said resistance value of said reference heater at said predetermined temperature is selected as said compensating resistance from said map.

9. In an oxygen concentration-sensing device including an oxygen concentration-sensing element for sensing the concentration of oxygen contained in a gas, a heater for heating said element, control means electrically connected to said heater for controlling the supply of electricity to said heater so as to bring the temperature of said heater to a desired temperature, and a coupler connecting said oxygen concentration-sensing element and said control means, the improvement comprising a compensating resistance accommodated in said coupler and having a resistance value corresponding to a resistance value of said heater assumed at said desired temperature, and wherein said control means comprises current supply means for supplying current to said heater, a comparator for controlling aid current supply means and having two input terminals, and a bridge circuit having a first series circuit formed by said heater and a first resistance serially connected to said heater, a junction between said heater and said first reference resistance being connected to one of said input terminals of said comparator, and a second series circuit formed by second and third resistances and connected in parallel with said first series circuit, a junction between said second and third resistances being connected to the other of said input terminals of said comparator, said compensating resistance comprising a fourth resistance connected in parallel to one of said second and third resistances.

10. An oxygen concentration-sensing device as claimed in claim 9, wherein said compensating resistance has a resistance value corresponding to a difference between an actual resistance value assumed by said heater at a predetermined temperature and a resistance value assumed by a reference heater at said predetermined temperature.

11. In an oxygen concentration-sensing device including at least one oxygen concentration-sensing element formed by an oxygen-pumping element and a cell element, each of said oxygen-pumping element and said cell element composed of a member formed of a solid electrolytic material having oxygen ion-conductivity, and a pair of electrodes having said member interposed therebetween, said oxygen-pumping element and said cell element defining a gas diffusion-limiting zone, a heater for heating said oxygen concentration-sensing element, and control means electrically connected to said heater for controlling the supply of electricity to said heater so as to bring the temperature of said heater to a desired temperature, the improvement comprising a circuit element having a circuit constant corresponding to a resistance value of said heater assumed at said desired temperature, and means for applying a given level of voltage to said circuit element, and wherein said control means comprises means for supplying electricity to said heater, and means for determining the amount of electricity so be supplied to said heater from an amount of current flowing through said circuit element when said said given level of voltage is applied to said circuit element.

12. An oxygen concentration-sensing device as claimed in claim 11, wherein said circuit element comprises a compensating resistance having a resistance value corresponding to the resistance value assumed by said heater at said desired temperature.

13. An oxygen concentration-sensing device as claimed in claim 12, including a second resistance, serially connected to said compensating resistance, said means for applying said given level of voltage to said circuit element applying said given level of voltage to said compensating resistance and said second resistance, and wherein said means for determining the amount of electricity to be supplied to said heater comprises means for reading in information on a voltage developed at a junction between said compensating resistance and said second resistance when said given level of voltage is applied thereto, and an amount of current flowing through said heater and a voltage developed across said heater when supplied with said electricity, as first data and second data, respectively, means for calculating a resistance value of said heater from said second data read in, means for correcting one of said resistance value calculated and a reference resistance value assumed by said heater at said desired temperature by said first data read in, and means for determining a duty ratio corresponding to a difference between said corrected one of said resistance value calculated and said reference resistance value, and the other of same, and wherein said means for supplying electricity to said heater supplies electricity to said heater in an amount determined by said duty ratio determined.

14. An oxygen concentration-sensing device as claimed in claim 12 or claim 13 wherein said control means has a map comprising a plurality of resistance values corresponding respectively to a plurality of predetermined differences between a plurality of predetermined resistance values which can be assumed by said heater at a predetermined temperature and a resistance value assumed by a reference heater at said predetermined temperature, and a plurality of correction values corresponding respectively to said plurality of resistance values, a resistance having a resistance value corresponding to a difference between an actual resistance value of said heater at said predetermined temperature and said resistance value of said reference heater at said predetermined temperature is selected as said compensating resistance from said map.

15. In an oxygen concentration-sensing device including at least one oxygen concentration-sensing element formed by an oxygen-pumping element and a cell element, each of said oxygen-pumping element and said cell element composed of a member formed of a solid electrolytic material having oxygen ion-conductivity, and a pair of electrodes having said member interposed therebetween, said oxygen-pumping element and said cell element defining a gas diffusion-limiting zone, a heater for heating said oxygen concentration-sensing element, and control means electrically connected to said heater for controlling the supply of electricity to said heater so as to bring the temperature of said heater to a desired temperature, the improvement comprising a compensating resistance having a resistance value corresponding to a resistance value of said heater assumed at said desired temperature, and wherein said control means comprises a plurality of resistances, at least one of which is connected in parallel with said compensating resistance, said resistances forming a bridge circuit in cooperation with said heater, and potential balance-maintaining means for controlling the amount of electricity to be supplied to said heater and maintaining potential balance of said bridge circuit.

16. An oxygen concentration-sensing device as claimed in claim 15, wherein said balance-maintaining means comprises current supply means for supplying current to said heater, and a comparator for controlling said current supply means and having two input terminals, said bridge circuit haing a first series circuit formed by said heater and a first resistance serially connected to said heater, a junction between said heater and said first reference resistance being connected to one of said input terminals of said comparator, and a second series comprising a fourth resistance connected in parallel to one of said second and third resistances.

17. An oxygen concentration-sensing device as claimed in claim 15, wherein said compensating resistance has a resistance value corresponding to a difference between an actual resistance value assumed by said heater at said predetermined temperature and a resistance value assumed by a reference heater at said predetermined temperature.

* * * * *